(12) United States Patent
Luo

(10) Patent No.: US 12,060,550 B1
(45) Date of Patent: Aug. 13, 2024

(54) FERMENTATION DEVICE, PLANTING SYSTEM, AND FERMENTATION METHOD

(71) Applicant: SHENZHEN CHENGXIN ENVIRONMENTAL PROTECTION TECHNOLOGY CO., LTD, Shenzhen (CN)

(72) Inventor: Chengxin Luo, Shenzhen (CN)

(73) Assignee: SHENZHEN CHENGXIN ENVIRONMENTAL PROTECTION TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/463,781

(22) Filed: Sep. 8, 2023

(30) Foreign Application Priority Data

Apr. 12, 2023 (CN) .......................... 202310415572.5

(51) Int. Cl.
*C12M 1/06* (2006.01)
(52) U.S. Cl.
CPC .................. *C12M 27/06* (2013.01)
(58) Field of Classification Search
CPC ....................................................... C12M 27/06
See application file for complete search history.

(56) References Cited

U.S. PATENT DOCUMENTS

| | | | | |
|---|---|---|---|---|
| 3,822,179 A * | 7/1974 | Chari et al. | ............ | D21C 3/228 |
| | | | | 162/49 |
| 4,198,211 A * | 4/1980 | Shattock | ................ | C12M 23/58 |
| | | | | 210/603 |
| 7,290,669 B1 * | 11/2007 | Hansen | ................... | C12M 23/36 |
| | | | | 210/629 |
| 2005/0089998 A1 * | 4/2005 | Miller | .................... | C12M 29/06 |
| | | | | 435/290.3 |
| 2007/0190643 A1 * | 8/2007 | Noll | .................... | F26B 11/0477 |
| | | | | 435/290.3 |
| 2010/0024809 A1 * | 2/2010 | Burke | .................... | C12M 33/16 |
| | | | | 127/1 |
| 2011/0239716 A1 * | 10/2011 | Miyanouchi | ........... | C12M 41/34 |
| | | | | 71/8 |
| 2014/0083939 A1 * | 3/2014 | Nguyen | ................. | C12M 45/03 |
| | | | | 210/612 |
| 2016/0229728 A1 * | 8/2016 | McPherson | ............. | F26B 17/04 |
| 2018/0016541 A1 * | 1/2018 | Hollah | .................... | C12M 21/04 |
| 2022/0324768 A1 * | 10/2022 | Hoff | ........................ | C05F 1/002 |

FOREIGN PATENT DOCUMENTS

WO   WO-2004053408 A1 * 6/2004   ................ C05F 3/00

* cited by examiner

*Primary Examiner* — William H. Beisner
*Assistant Examiner* — Danielle B Henkel
(74) *Attorney, Agent, or Firm* — Daniel M. Cohn; Howard M. Cohn

(57) ABSTRACT

A fermentation device includes a fermenter. The fermenter includes a tank, augers, and a motor. The tank is horizontally arranged. A first end of the tank is connected with a material feeding port. A second end of the tank is connected with a material discharging port. A height of the material discharging port is not less than a height of the tank. Liquid raw material and solid raw material are added into the tank from the material feeding port. The augers are arranged in the tank. Each of the augers includes a central shaft and a blade. An inner edge of each blade is connected with a corresponding central shaft. A gap is defined between an outer edge of each blade and inner walls of the tank. The motor is connected with the augers and drives the augers to rotate in a first direction or a second direction.

9 Claims, 5 Drawing Sheets

FERMENTATION DEVICE, PLANTING SYSTEM, AND FERMENTATION METHOD

TECHNICAL FIELD

The present disclosure relates to a field of fermentation technology, and in particular to a fermentation device, a planting system, and a fermentation method.

BACKGROUND

Fermentation devices are used in many fields such as waste utilization, fertilizer preparation, food preparation, etc. The Chinese patent No. CN215279117U discloses a stirring fermentation device capable of turning materials up and down, which comprises a fermenter main body. A turning auger is installed in the fermenter main body, and the turning auger continues to turn the materials. Then fermented mature products are discharged out of the fermenter main body. However, the stirring fermentation device is unable to achieve fermentation of the materials during a transportation process.

SUMMARY

In view of this, it is necessary to provide a fermentation device, a planting system and a fermentation method, which realize discharge of a finished fermentation product while realizing fermentation during a transportation process.

The present disclosure provides the fermentation device configured to mix liquid raw material and solid raw material and gradually fermented the liquid raw material and the solid raw material into a liquid fermentation product. The fermentation device comprises a fermenter. The fermenter comprises a tank, augers, and a motor.

The tank is horizontally arranged. A first end of the tank is connected with a material feeding port. A second end of the tank is connected with a material discharging port. A height of the material discharging port is not less than a height of the tank. The liquid raw material and the solid raw material are added into the tank from the material feeding port.

The augers are arranged in the tank. Each of the augers comprises a central shaft and a blade. An inner edge of each blade is connected with a corresponding central shaft. A gap is defined between an outer edge of each blade and inner walls of the tank.

The motor is connected with the augers and drives the augers to rotate in a first direction or a second direction. When the augers rotate in the first direction, the liquid raw material and the solid raw material move from the material feeding port towards the material discharging port. When the augers rotate in the second direction, the liquid raw material and the solid raw material move from the material discharging port towards the material feeding port.

Furthermore, a first end of each central shaft of each of the augers is fixed, and a second end of each central shaft is a free end. The free end of each central shaft is capable of fluttering in the tank by the liquid raw material and the solid raw material in the tank.

Furthermore, the augers are made of plastic.

Furthermore, the tank comprises tank units. One end of each of the tank units is connected with one end of an adjacent tank unit of the tank units through an aisle. Each of the augers is arranged in a corresponding tank unit of the tank units.

Furthermore, the fermenter comprise gears. Each of the augers arranged in the corresponding tank units are connected with a corresponding gear of the gears. The gears are engaged end by end. One of the gears is driven to rotate by the motor.

Furthermore, the fermentation device further comprises a liquid raw material storage box, a solid raw material storage bin, and a liquid fermentation product storage box. The liquid raw material storage box is connected with the material feeding port. The solid raw material storage box is connected with the material feeding port. The liquid fermentation product storage box is connected with the material discharging port.

The present disclosure provides the fermentation method implemented by the fermentation device. The fermentation method comprises:

step 1: continuously and synchronously adding the liquid raw material and the solid raw material from the material feeding port while slowly driving the augers, by the motor, to rotate a first number of turns in the first direction so as to move the liquid raw material and the solid raw material forward by a certain distance $L1$, where a distance from the material feeding port to the material discharging port is $L2$; $L1=L2/n$, and N is an integer not less than 2;

step 2: stopping adding the liquid raw material and the solid raw material, slowly driving the augers, by the motor, to rotate a second number of turns in the second direction, where the second number of turns is equal to the first number of turns;

step 3: slowly driving the augers, by the motor, to rotate in the first direction by the first number of turns; and step 4: repeating the step 1 to step 3 after a predetermined period of time.

The present disclosure provides the fermentation method implemented by the fermentation device. The fermentation method comprises:

step 1: continuously and synchronously adding the liquid raw material and the solid raw material from the material feeding port while slowly driving the augers, by the motor, to rotate a first number of turns in the first direction so as to move the liquid raw material and the solid raw material forward by a certain distance $L1$, where a distance from the material feeding port to the material discharging port is $L2$; $L1<L2$;

step 2: stopping adding the liquid raw material and the solid raw material, slowly driving the augers, by the motor, to rotate a second number of turns in the second direction, where the second number of turns is less than the first number of turns;

step 3: slowly driving the augers, by the motor, to rotate the first number of turns in the first direction; and step 4: repeating the step 1 to step 3 after a predetermined period of time.

Furthermore, a time interval from a current step 1 to a next step 1 is t. Time required for the liquid raw material and the solid raw material to be mixed and completely fermented into the liquid fermentation product is T. t is not less than $L1 \times T/L2$.

The present disclosure provides the planting system. The planting system comprises a planting area and the fermentation device. The liquid fermentation product is supplied to the planting area.

Compared with the prior art, the present disclosure is suitable for mixed fermentation of the liquid raw material and the solid raw material. The liquid raw material and solid raw material are synchronously added into the tank from the material feeding port. When the augers rotate in the first direction, the liquid raw material and the solid raw material are driven to move forward. When the augers rotate in the second direction, the liquid raw material and the solid raw material are driven to move backward. A space between the blade of the each of the augers and the tank is served as a fermentation space unit. The present disclosure realizes discharge of the liquid fermentation product while realizing the fermentation of the liquid raw material and the solid raw material during the conveying process.

DETAILED DESCRIPTION

Figure 1:
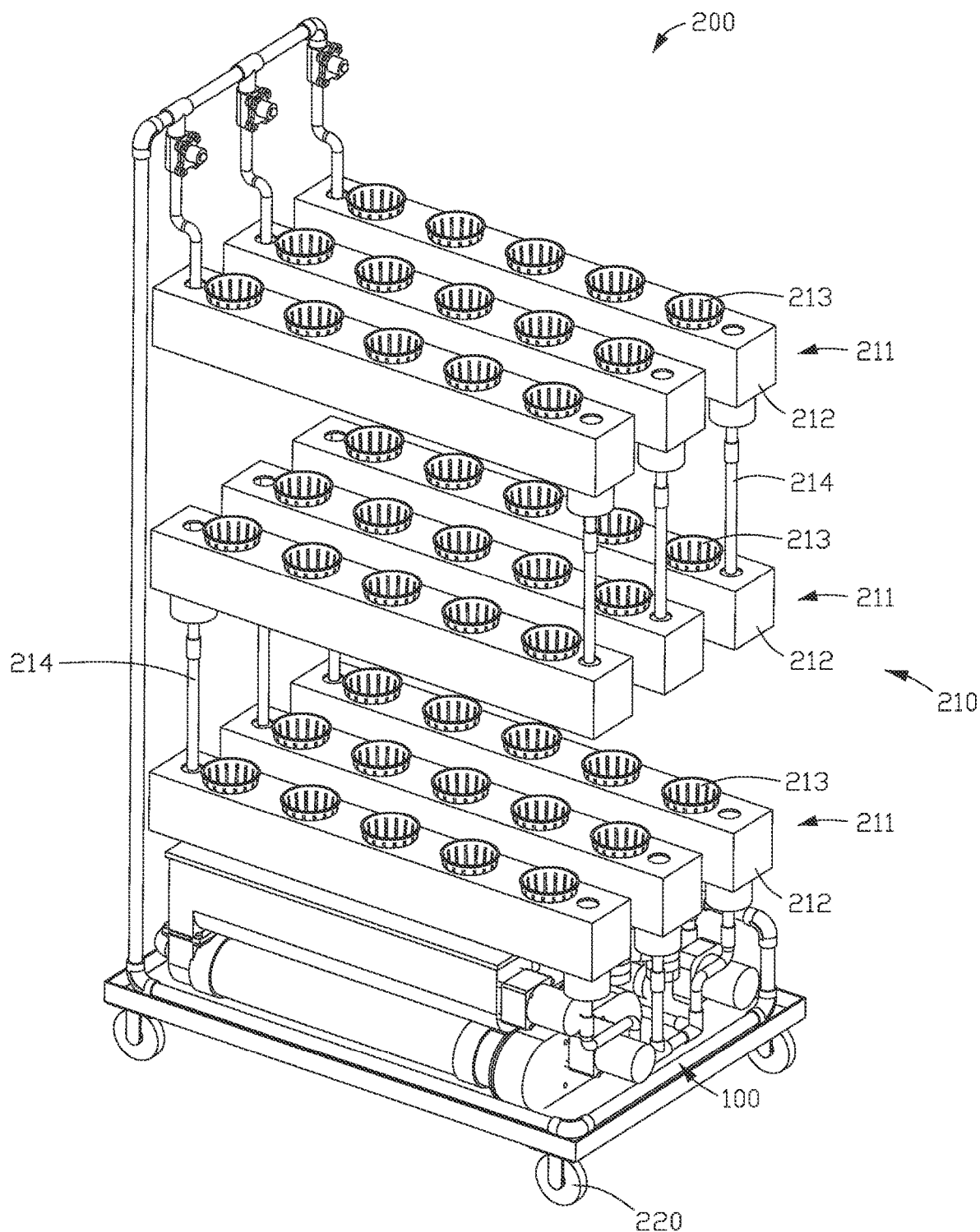
FIG. 1 is a structural schematic diagram of a planting system according to one embodiment of the present disclosure.

Technical solutions in the embodiments of the present disclosure will be clearly and completely described below in conjunction with the accompanying drawings in the embodiments of the present disclosure. Obviously, the described embodiments are only a part of the embodiments of the present disclosure, rather than all of the embodiments. Based on the embodiments of the present disclosure, all other embodiments obtained by those of ordinary skill in the art without creative work shall fall within the protection scope of the present disclosure. It is understood that the drawings are only provided for reference and illustration, and are not used to limit the present disclosure. The connection relationship shown in the drawings is only for the convenience of clear description, and does not intend to limit the connection mode.

It should be noted that when a component is considered to be "connected" to another component, it can be directly connected with another component, or there may be a centered component at the same time. Unless otherwise defined, all technical and scientific terms used herein have the same meaning as commonly understood by those skilled in the art of the present disclosure. It should be noted in the description of the present disclosure that, unless otherwise regulated and defined, terms such as "installation", "bonded", and "connection" shall be understood in broad sense, and for example, may refer to fixed connection or detachable connection or integral connection; may refer to mechanical connection or electrical connection; and may refer to direct connection or indirect connection through an intermediate medium or inner communication of two elements. For those of ordinary skill in the art, the meanings of the above terms in the present disclosure may be understood according to concrete conditions.

In addition, it should be noted that in the description of the present disclosure terms such as "central", "horizontal", "upper", "lower", "left", "right", "vertical", "horizontal", "top", "bottom", "inner", "outer", etc. indicate direction or position relationships shown based on the drawings, and are only intended to facilitate the description of the present disclosure and the simplification of the description rather than to indicate or imply that the indicated device or element must have a specific direction or constructed and operated in a specific direction, and therefore, shall not be understood as a limitation to the present disclosure. In addition, terms such as "first", "second", and "third" are only used for the purpose of description, rather than being understood to indicate or imply relative importance.

As shown in FIG. 1, a fermentation device 100 is applied to a planting system 200. The planting system 200 comprises a planting area 210 and the fermentation device 100. The planting area 210 comprises planting layers 211. Each of the planting layers 211 comprises planting tanks 212. Planting baskets 213 are arranged in the planting tanks 212. The planting tanks 212 on an upper planting layer of each two adjacent planting layers of the planting layers are one-to-one connected with the planting tanks 212 on a lower planting layer of each two adjacent planting layers of the planting layers through pipelines 214. An upper end of each of the pipelines 214 is inserted into a corresponding planting tank of the planting tanks 212 on the upper planting layer of each two adjacent planting layers of the planting layers upper planting tank 212 and exceeds a bottom of the corresponding planting tank of the planting tanks 212. The fermentation device 100 is arranged below the planting area 210. The liquid fermentation product fermented by the fermentation device 100 is transported to the planting tanks 212 on an uppermost planting layer of the planting layers through a pump. After the liquid fermentation product in the planting tanks 212 on the uppermost planting layer reaches a certain height, the liquid fermentation product enters the planting tanks 212 on other lower planting layers by siphon.

The planting system 200 further comprises a walking device 220 to realize moving of the planting system 200.

Figure 2:
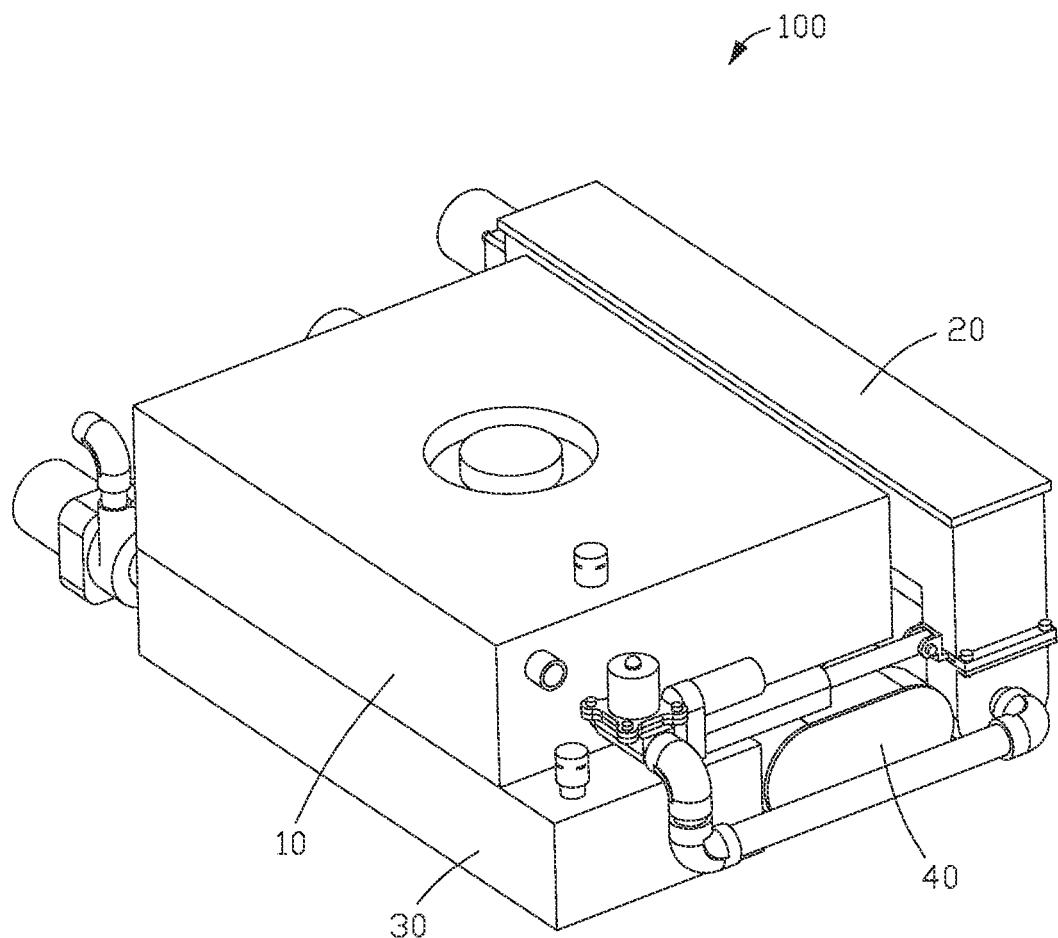
FIG. 2 is a structural schematic diagram of a fermentation device according to one embodiment of the present disclosure.

As shown in FIG. 2, the fermentation device comprises a liquid raw material storage box 10, a solid raw material storage bin 20, a liquid fermentation product storage box 30, and a fermenter 40. The liquid raw material storage box 10, the solid raw material storage bin 20, the liquid fermentation product storage box 30, and the fermenter 40 are stacked in a modular manner to form the fermentation device in a shape similar to a cuboid to fully utilize space.

Specifically, the liquid raw material storage box 10 and the solid raw material storage bin 20 are arranged side by side, and the fermentation product storage box 30 and the fermenter 40 are arranged side by side under the liquid raw material storage box 10 and the solid raw material storage bin 20.

Figure 4:
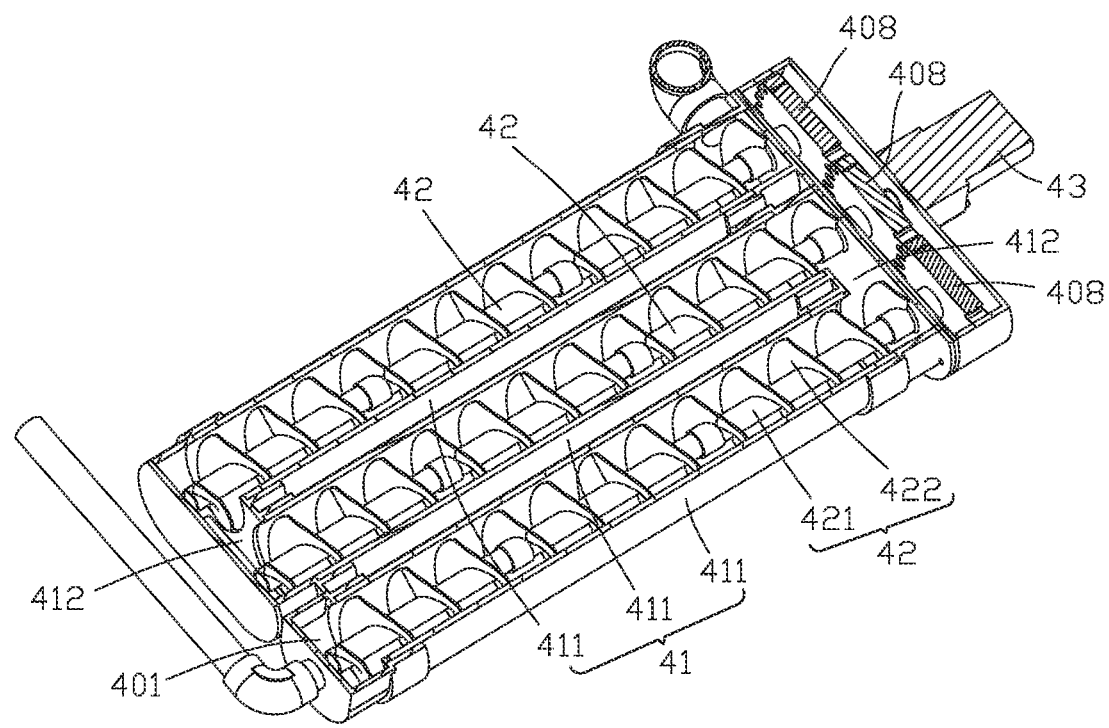
FIG. 4 is a horizontal cross-sectional schematic diagram of a fermenter according to one embodiment of the present disclosure.
Figure 5:
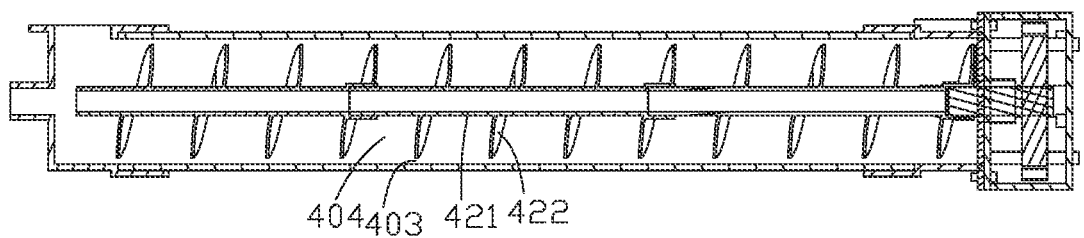
FIG. 5 is a vertical cross-sectional schematic diagram of the fermenter according to one embodiment of the present disclosure.

The liquid raw material storage box 10 and the solid raw material storage box 20 is connected with a material feeding port of the fermenter 40 (as shown in FIG. 4).

Figure 3:
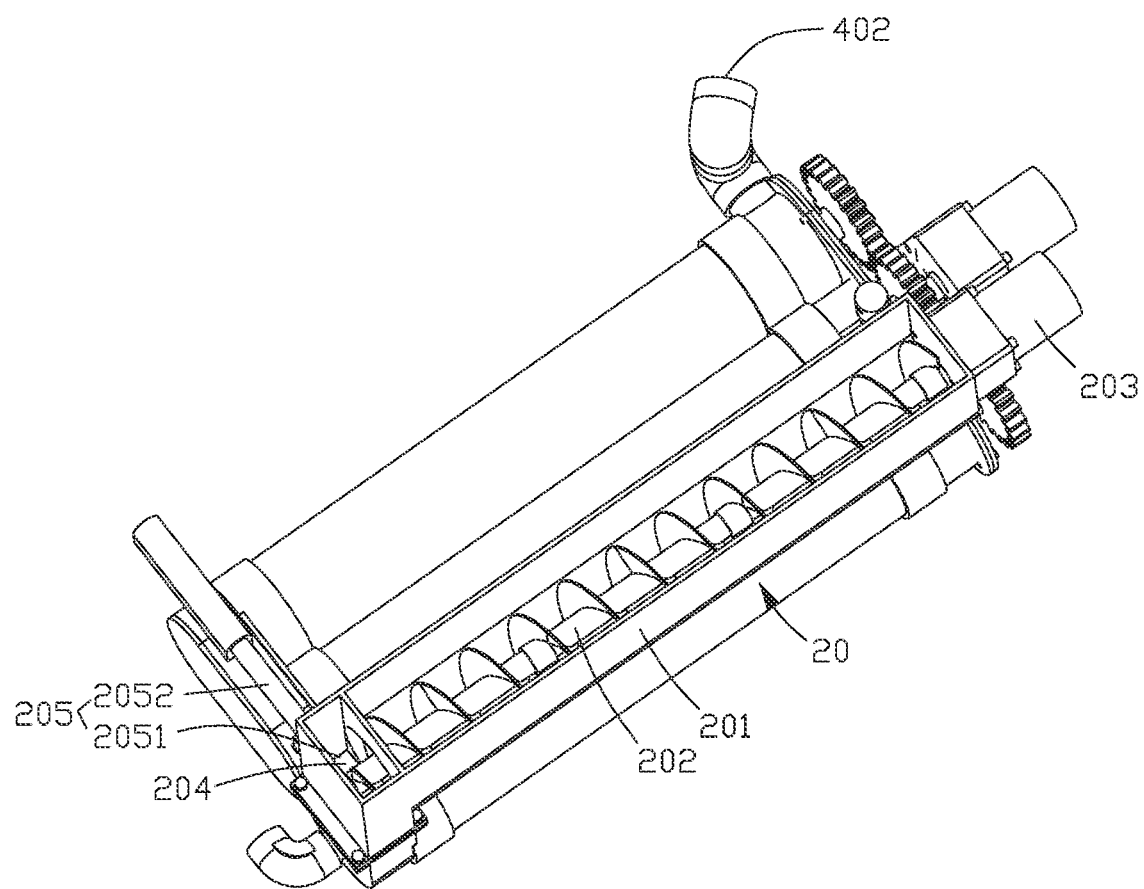
FIG. 3 is a structural schematic diagram of a solid raw material storage bin according to one embodiment of the present disclosure.

The liquid fermentation product storage box 30 is connected with a material discharging port of the fermenter 40 (as shown in FIG. 3). The liquid raw material storage box 10 may be further connected with the liquid fermentation product storage box 30.

As shown in FIG. 3, the solid raw material storage bin 20 comprises a bin body 201, a twist drill 202 is arranged in the bin body 201. The twist drill 202 is connected with a driving motor 203. The twist drill 202 is driven to rotate by the driving motor 203. An end portion of the bin body 201 defines an outlet 204. The outlet 204 is connected with an outlet opening and closing device 205. The outlet opening and closing device 205 comprises a door 2051 and a cylinder 2052. The cylinder 2052 drives the door to move so as to realize opening and closing of the outlet 204.

As shown in FIG. 4, the fermenter 40 comprises a tank 41, augers 42, and a motor 43. A first end of the tank 41 is connected with the material feeding port 401. The material feeding port 401 is arranged below the outlet 204. A second end of the tank 41 is connected with the material discharging port 402. A height of the material discharging port 402 is not less than a height of the tank 41. The material discharging port 402 is arranged on a pipe connected with the tank 41 or on a top of the tank 41. The augers 42 are arranged in the tank 41. The motor 43 drives the augers to rotate. The motor 43 rotates forward or reversely rotates to drive the augers 42 to rotate in a first direction or in a second direction. When the augers 42 rotate in the first direction, the liquid raw material and the solid raw material move from the material feeding port 401 towards the material discharging port 402. When the augers 42 rotate in the second direction, the liquid raw material and the solid raw material move from the material discharging port 402 towards the material feeding port 401.

In one specific embodiment, the tank 41 comprises tank units 411 that are horizontally arranged. One end of each of the tank units 411 is connected with one end of an adjacent tank unit of the tank units through an aisle 412 to form a channel. Each of the augers 42 is arranged in a corresponding tank unit of the tank units.

The tank 41 is divided into the tank units 411, making the tank 41 short, which facilitates installation of the fermenter 40 is a narrow space. Specifically, the tank units 411 are arranged in parallel in a row. An outlet end of any one of the tank units 411 and an inlet end of an adjacent tank unit of the tank units 411 are arranged on the same side. The outlet end of any one of the tank units 411 and the inlet end of the adjacent tank unit are connected through a corresponding aisle 412.

Each of the augers 42 arranged in the corresponding tank units 411 comprises a central shaft 421 and a blade 422. An inner edge of each blade 422 is connected with a corresponding central shaft 421 and no gap is defined. A gap 403 is defined between an outer edge of each blade 422 and inner walls of the tank 41. A space 404 is defined between each blade 422 and the corresponding central shaft 421, which forms a fermentation space unit.

A first end of each central shaft of each of the augers 42 arranged in the corresponding tank unit 411 is mounted on an end wall of the corresponding tank unit 411 and is rotatably connected with the end wall of the corresponding tank unit 411. Each central shaft 421 is fixed through fixing of the first end thereof. Gears 408 are provided. The first end of each central shaft is connected with a corresponding gear of the gears 408. The gears 408 are engaged end by end. One of the gears 408 is driven to rotate by the motor 43.

A second end of each central shaft 421 is a free end that is nit fixed and is able to flutter by the liquid raw material and the solid raw material in the tank 41. In the embodiment, the augers 42 are made of plastic, which facilitates fluttering of the augers 42. After the liquid raw material and the solid raw material are simultaneously added to the tank 41 through the material feeding port 401, liquid (such as the liquid raw material and the liquid fermentation product) and the gap 403 between each blade 422 and the tank 41 allows the free end of each of the augers 42 to flutter in the tank 41. Especially when the motor 43 drives the augers to rotate, the free end of each of the augers also flutters due to eccentric force.

Since in a mixed fermentation process of the solid raw material and the liquid raw material, precipitation of viscous slag material is generated. Each blade 422 flutters to rub the inner walls of the tank 41, and a portion of the viscous slag material on the inner walls of the tank 41 is rubbed to be fermented, so that the fermentation of the solid raw material and the liquid raw material is sufficient.

In one specific embodiment, the present disclosure provides a fermentation method implemented by the fermentation device. The fermentation method comprises:

step 1: continuously and synchronously adding the liquid raw material and the solid raw material from the material feeding port 401 while slowly driving the augers 42, by the motor 43, to rotate a first number of turns in the first direction so as to move the liquid raw material and the solid raw material forward by a certain distance L1, where a distance from the material feeding port to the material discharging port is L2; L1=L2/n, and N is an integer mot less than 2;

In the process, the augers 42 slowly rotate the first number of turns, the solid raw material and the liquid raw material are uniformly distributed transversely in a section having the certain length L1. Each section is in the space between each blade and each central shaft. Mixture formed by gradually mixing the solid raw material and the liquid raw material in the space of the certain length L1 is regarded as a first-stage fermentation product.

step 2: stopping adding the liquid raw material and the solid raw material, slowly driving the augers 42, by the motor 43, to rotate a second number of turns in the second direction; where the second number of turns is equal to the first number of turns;

The augers 42 reversely rotate so that the solid raw material and the liquid raw material are fully mixed.

step 3: slowly driving the augers, by the motor, to rotate the first number of turns in the first direction; and step 4: repeating the step 1 to step 3 after a predetermined period of time.

In this way, there are n sections of fermentation products in the tank 41, and the first-stage fermentation product, a second-stage fermentation product, and an $n^{th}$-stage fermentation product are sequentially formed from a rear section of the sections to a front section of the sections. After repeating the step 1 to step 3 for n+1 times, the n-stage fermentation product is discharged out of the fermenter 40.

Fermentation degrees of the fermentation products in the n sections are different. The closer the fermentation products to the material discharging port, the greater the fermentation degree of the fermentation products. That is, the more liquid raw material is contained in the fermentation products, the closer the fermentation products to the material feeding port 401, and the more liquid fermentation product and the less liquid material are contained in the fermentation products closer to the material discharging port 402. In a last section of the sections (i.e., a foremost section of the sections), the fermentation product is almost the liquid fermentation product.

It should be noted that since there is the gap 403 between the outer edge of each blade 422 and the inner walls of the tank 41, in a rotation process, the liquid raw material that is not fully mixed and the liquid fermentation product formed by fermentation moves in each gap 403. In the step I, when the augers 42 rotate in the first direction, due to continuous addition of the liquid raw material, under an action of a front-end hydraulic pressure, a part of the liquid raw material in the fermentation product in the rear section or the liquid fermentation product originally fermented and produced in the rear section of the tank 41 continuously moves into the fermentation product in the front section, so that the liquid fermentation product almost completely flows out of the tank 41 under the action of the front-end hydraulic pressure in the foremost section. Therefore, in a process of executing the step 1, the quid fermentation product fermented at the foremost section is discharged to the liquid fermentation product storage box 30.

In a case that the liquid raw material is not continuously added, the augers 42 slowly rotate in the first direction (forward), the liquid fermented product fermented in the foremost section cannot be discharged, and the augers 42 slowly rotate in the first direction to increase the front-end hydraulic pressure of the foremost section, so that the liquid raw material that is not fully mixed and the liquid fermentation product formed by fermentation in the rear section cannot move towards the front section, the liquid raw material that is not fully mixed and the liquid fermentation product formed by fermentation flow back through the gap 403 between the outer edge of each blade 422 and the inner walls of the tank 41, and the viscous slag material not completely fermented moves forwards or backwards along with the augers 42 and is mixed with the liquid raw material that is not fully mixed and the liquid fermentation product formed by fermentation. Similarly, when the augers 42 slowly rotate in the second direction (backward), the fermentation product in a last section of the sections hinders liquid in the front section, so that the liquid in the front section is unable to move to the rear section, and the liquid raw material that is not fully mixed and the liquid fermentation product formed by fermentation flows back through the gap 403 between the outer edge of each blade 422 and the inner walls of the tank 41.

Another embodiment of present disclosure provides the fermentation method implemented by the fermentation device. The fermentation method comprises:

step 1: continuously and synchronously adding the liquid raw material and the solid raw material from the material feeding port 401 while slowly driving the augers 42, by the motor 43, to rotate a first number of turns in the first direction, so as to move the liquid raw material and the solid raw material forward by a certain distance L1, where a distance from the material feeding port 401 to the material discharging port 402 is L2; L1<L2;

step 2: stopping adding the liquid raw material and the solid raw material, slowly driving the augers 42, by the motor 43, to rotate a second number of turns in the second direction, where the second number of turns is less than the first number of turns;

step 3: slowly driving the augers 42, by the motor 43, to rotate the first number of turns in the first direction; and Step 4: repeating the step 1 to step 3 after a predetermined period of time.

Furthermore, a time interval from a current step 1 to a next step 1 is t. Time required for the liquid raw material and the solid raw material to be mixed and completely fermented into the liquid fermentation product is T. t is not less than L1×T/L2. Therefore, in a process of repeating the step 1 to step 3, the first-stage fermentation product gradually moves to the material discharging port 402. At this time, the first-stage fermentation product is naturally fermented into the liquid fermentation product in a forward moving process, and the liquid fermentation product is discharged out of the fermenter 40.

In the specification and claims of the present disclosure, terms "comprise/comprise" and terms "have/contain" and their variants are used to designate existence of stated features, values, steps or components, but do not exclude the existence or addition of one or multiple other features, values, steps, components, or combinations thereof.

For clarity of explanation, some features of the present disclosure are described in different embodiments. However, these features can also be combined and described in a single embodiment. Moreover, some features of the present disclosure are only described in a single embodiment for the sake of brevity. However, these features can also be described in different embodiments separately or in any suitable combination.

Foregoing descriptions are only optional embodiments of the present disclosure and are not intended to limit the present disclosure. Any modification, equivalent replacement, or improvement within the technical scope of the present disclosure should be comprised in the protection scope of the present disclosure.

What is claimed is:

1. A fermentation device configured to mix liquid raw material and solid raw material and gradually ferment the liquid raw material and the solid raw material into a liquid fermentation product, comprising: a fermenter;
   wherein the fermenter comprises a tank, augers, and a motor;
   wherein the tank is horizontally arranged; a first end of the tank is connected with a material feeding port; a second end of the tank is connected with a material discharging port; a height of the material discharging port is not less than a height of the tank; the liquid raw material and the solid raw material are added into the tank from the material feeding port;
   wherein the augers are horizontally arranged in the tank; each of the augers comprises a central shaft and a blade; an inner edge of each blade is connected with a corresponding central shaft; a gap is defined between an outer edge of each blade and inner walls of the tank, wherein a first end of each central shaft of each of the augers is fixed, and a second end of each central shaft is a free end; the free end of each central shaft is capable of fluttering in the tank by the liquid raw material and the solid raw material in the tank, each blade flutters to rub the inner walls of the tank, and a portion of the viscous slag material on the inner walls of the tank is rubbed to be fermented; and
   wherein the motor is connected with the augers and drives the augers to rotate in a first direction or a second direction; when the augers rotate in the first direction, the liquid raw material and the solid raw material move from the material feeding port towards the material discharging port; when the augers rotate in the second direction, the liquid raw material and the solid raw material move from the material discharging port towards the material feeding port.

2. The fermentation device according to claim 1, wherein the augers are made of plastic.

3. The fermentation device according to claim 1, wherein the tank comprises tank units, one end of each of the tank units is connected with one end of an adjacent tank unit of the tank units through an aisle; each of the augers is arranged in a corresponding tank unit of the tank units.

4. The fermentation device according to claim 3, wherein the fermenter comprise gears; each of the augers arranged in the corresponding tank units are connected with a corresponding gear of the gears; the gears are engaged end by end; one of the gears is driven to rotate by the motor.

5. The fermentation device according to claim 1, wherein the fermentation device further comprises a liquid raw material storage box, a solid raw material storage bin, and a liquid fermentation product storage box; the liquid raw material storage box is connected with the material feeding port; the solid raw material storage box is connected with the material feeding port; the liquid fermentation product storage box is connected with the material discharging port.

6. A fermentation method implemented by the fermentation device according to claim 1, comprising:
   step 1: continuously and synchronously adding the liquid raw material and the solid raw material from the material feeding port while slowly driving the augers, by the motor, to rotate a first number of turns in the first direction so as to move the liquid raw material and the solid raw material forward by a certain distance L1, wherein a distance from the material feeding port to the material discharging port is L2; L1–L2/n, and N is an integer mot less than 2;
   step 2: stopping adding the liquid raw material and the solid raw material, slowly driving the augers, by the motor, to rotate a second number of turns in the second direction; wherein the second number of turns is equal to the first number of turns;
   step 3: slowly driving the augers, by the motor, to rotate the first number of turns in the first direction; and
   step 4: repeating the step 1 to step 3 after a predetermined period of time.

7. A fermentation method implemented by the fermentation device according to claim 1, comprising:
   step 1: continuously and synchronously adding the liquid raw material and the solid raw material from the material feeding port while slowly driving the augers, by the motor, to rotate a first number of turns in the first direction to move the liquid raw material and the solid raw material forward by a certain distance L1, wherein a distance from the material feeding port to the material discharging port is L2; L1<L2;
   step 2: stopping adding the liquid raw material and the solid raw material, slowly driving the augers, by the motor, to rotate a second number of turns in the second direction; wherein the second number of turns is less than the first number of turns;
   step 3: slowly driving the augers, by the motor, to rotate the first number of turns in the first direction; and
   step 4: repeating the step 1 to step 3 after a predetermined period of time.

8. The fermentation method according to claim 7, wherein a time interval from a current step 1 to a next step 1 is t; time required for the liquid raw material and the solid raw material to be mixed and completely fermented into the liquid fermentation product is T; t is not less than L1×T/L2.

9. A planting system, comprising a planting area and the fermentation device according to claim 1; the liquid fermentation product is supplied to the planting area.

* * * * *